(12) United States Patent
Bhatti

(10) Patent No.: US 8,142,766 B1
(45) Date of Patent: Mar. 27, 2012

(54) HAIR REMOVAL GEL COMPOSITION

(76) Inventor: Yasmin Azra Bhatti, Allentown, PA (US)

( * ) Notice: Subject to any disclaimer, the term of this patent is extended or adjusted under 35 U.S.C. 154(b) by 177 days.

(21) Appl. No.: 12/590,538

(22) Filed: Nov. 10, 2009

(51) Int. Cl.
*A61K 8/00* (2006.01)
*A61K 8/19* (2006.01)
*C14C 1/06* (2006.01)

(52) U.S. Cl. ............... 424/70.1; 424/73; 8/161; 8/94.16

(58) Field of Classification Search .................. None
See application file for complete search history.

(56) References Cited

U.S. PATENT DOCUMENTS 4,832,949 A * 5/1989 Royal .............................. 424/73

OTHER PUBLICATIONS

About-Hair-Removal, archived Feb. 5, 2002, "http://web.archive.org/web/20020205113152/http://about-hair-removal.com/sugaring-recipes.htm", pp. 1-2.*
Honey Nutrition Facts, Benefits of BHoney, accessed Sep. 28, 2011,"http://www.benefits-of-honey.com/honey-nutrition.html", pp. 1-3.*
Sugar-Pro, "Sugar-Pro hair removers", archived Jun. 4, 2003, available at http://web.archive.org/web/20030604225340/http://hair-removers.com/sugar-pro.html, pp. 1.*
"Waxing Courses Online" archive date Aug. 19, 2009, available at: http://www.waxingcourses.com/28/sugaring-for-hair-removalninas-technique, pp. 1-8.*
Yoga Health Benefits, "Hair Removal Methods: Bleaching | Sugaring | Waxing | Permanent Hair Removal", archived Aug. 27, 2009, available at: http://www.yogawiz.com/blog/home-remedies/sugaring-waxing-upper-lip-permanent-hair-removal-methods-bleaching-sugaring.html, pp.*

* cited by examiner

*Primary Examiner* — Michael G Hartley
*Assistant Examiner* — Lance Rider

(57) ABSTRACT

A gel composition for removal of unwanted human hair from human skin that is comprised of a mixture of a majority portion of sugar and minor portions of lemon juice and water. The portions of sugar and lemon juice are initially heated to an appropriate temperature over a sufficient duration at which time the minor portion of water is added to the mixture. After adding water to the first mixture, the second mixture with water is heated until a composition of gel-like consistency has been produced. The composition is applied by hand or utensil to a part of human skin with unwanted hair and then covered with an absorbent layer of cloth until the unwanted hair has been dissolved by the composition at which time the cloth is removed from the skin with the composition absorbed therein and unwanted hair attached thereon.

3 Claims, 2 Drawing Sheets

HAIR REMOVAL GEL COMPOSITION

BACKGROUND OF THE INVENTION

This version of the invention is concerned with the field of hair removal creams, solutions, and gel compositions. More specifically, this version of the invention is concerned with hair removal compositions in the form of gel compositions that are comprised of natural substances, which are stored and used directly at room temperature (instead of being refrigerated or heated) to remove unwanted hair by the roots from certain portions of the body.

Removal of hair from the skin for aesthetic and cosmetic purposes is generally accomplished by a variety of processes, which include but are not limited to shaving; hair-removing products in the form of liquids or creams; and extraction of hair follicles or strands from the skin by a variety of procedures, such as tweezers, hot waxes, and electrolysis. Shaving is a popular method but is generally least effective as the hair and hair root remaining within the skin are visible and grow back relatively quickly in a more pronounced appearance.

Liquids and creams generally consist of combinations of chemicals, such as calcium, strontium thioglycolate, or thiolactate to dissolve hair in either localized or expanded areas of the body. Again, the hair root remains, thereby requiring frequently successive treatments. In addition, it is not uncommon for the adjacent skin to become irritated or to develop a sensitivity or allergy to the product. The hair extraction method employing tweezers is a slow, tedious process, limited by the small grasping capacity of tweezers and is best applied to removal of hair from the nose and eyebrows. Hot wax coatings, which can remove hair over a greater area more quickly than tweezers, requires use of a wax heating and containment apparatus, which may not be amenable to use in the home or to function, in general, as a portable hair removal device. In addition, various wax compositions are prone to irritate and inflame the skin.

What is needed then to overcome the aforementioned disadvantages of conventional hair removing techniques, devices, crèmes, and solutions is the provision of a water-soluble hair removal gel composition that is comprised of natural ingredients and removes hair by the roots without irritating, inflaming, or causing an allergy in adjacent skin.

SUMMARY OF THE INVENTION

The present version of the invention, which will be described in greater detail hereinafter, relates to the field of hair removal creams, solutions, and gel compositions. More specifically, this version of the invention is concerned with hair removal compositions in the form of gel compositions that are comprised of natural substances, which are stored and used directly at room temperature (instead of being refrigerated or heated) to remove unwanted hair by the roots from certain portions of the body.

Described briefly, according to a typical embodiment, the invention presents a hair removal gel composition for application to a portion or limb of the body for removal of hair strands or follicles, including the roots thereof. It is comprised of 16 ounces of sugar and 3 ounces of lemon or limejuice, which are cooked at medium heat (200 deg F.). After some time, 2 ounces of water is gradually added to the mixture until it achieves a gel-like, even consistency. After an appropriate amount of time has elapsed for cooling, the mixture or gel composition can be deposited into a container for storage. In alternate versions of the gel composition, the amounts of sugar, lemon or limejuice, and water can be varied to vary the consistency of the gel composition, along with the addition of rose water or orange juice in varying amounts for inclusion of a fragrance. The finished gel composition can be applied to the skin by hand or with a utensil, such as a spoon, in the direction of hair growth. Removal of unwanted hair and the gel composition is accomplished by placing a cloth of absorbent material over the gel composition until the gel composition is substantially absorbed by the cloth, at which time the cloth is separated from the skin along with the gel composition and the hair dissolved by the gel composition.

My invention, therefore, resides not in any one of these features per se, but rather in the particular combination of all of them herein disclosed. It is distinguished from the prior art in this particular combination of all of its structures for the functions specified. In order that the detailed description of the invention may be better understood and that the present contribution to the art can be more fully appreciated, additional features of the invention will be described hereinafter. It should be appreciated by those skilled in the art that the conception and the disclosed specific methods and structures may be readily utilized as a basis for modifying of designing other compositions and methods for carrying out the same purposes of the present invention and that such equivalent compositions and methods do not depart from the spirit and scope of the invention.

OBJECTS OF THE INVENTION

Accordingly, it is an object of my version of the invention to provide a low-cost, easy-to-manufacture, and easy-to-market hair removal gel composition.

A further object of my version of the invention is to provide an easy-to-use and versatile hair removal gel composition.

A significant object of the invention is to provide a hair removal gel composition of natural ingredients, which consists of varying amounts of sugar; lemon juice, limejuice, or other citrus juice; and water that is heated and combined, along with certain fragrance-producing solutions as desired until a gel composition amenable to application upon the surface of the skin is produced.

A final but very significant object of the invention is to provide a water-soluble hair removal gel composition that is stored and applied to skin with unwanted hair directly at room temperature, said hair removal gel composition used with a cloth of absorbent material to remove hair by the roots without irritating, inflaming, or causing an allergy in adjacent skin.

Other objects and advantages of the present invention will become apparent from the following descriptions, taken in connection with the accompanying drawings, wherein, by way of illustration and example, various embodiments of the present invention are disclosed.

The drawings constitute a part of this specification and include exemplary embodiments to the invention, which may be embodied in various forms. It is to be understood that in some instances various aspects of the invention may be shown exaggerated or enlarged to facilitate an understanding of the invention.

Figure 1:
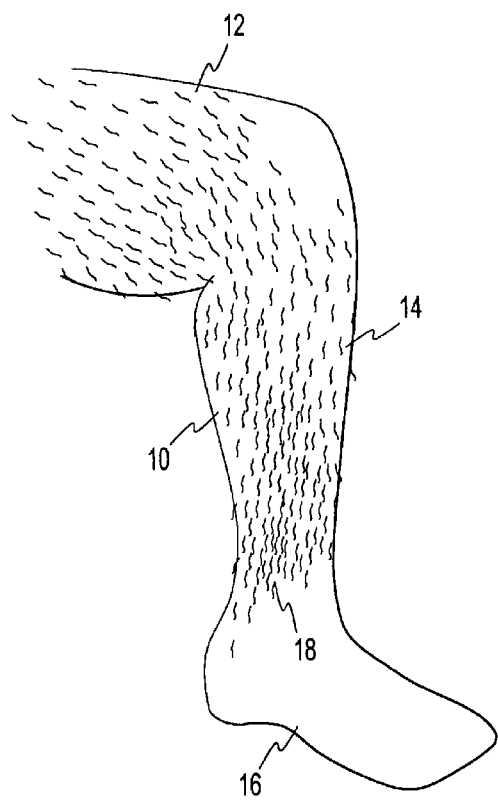
FIG. 1 is a perspective view of a bare leg covered with hair.

| DRAWING REFERENCE NUMERALS | |
|---|---|
| 10 | Leg |
| 12 | Upper Leg |
| 14 | Lower Leg |
| 16 | Foot |
| 18 | Hair Strands |
| 20 | Hair Removal Gel Composition |
| 22 | Cloth |
| 24 | Hairless Portion of Lower Leg |

DETAILED DESCRIPTION OF THE PREFERRED EMBODIMENTS

A detailed description of the preferred embodiments is provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed method or manner.

Referring now to the drawings and, in particular, to FIG. 1 wherein there is illustrated a bare leg 10 of a user. The major parts of the leg 10, namely the upper leg 12, lower leg 14, and foot 16, are shown for purposes of this disclosure, which conveys that any part of the human body covered with unwanted hair can receive application of the gel composition for removal there from of said hair. The upper 12 and lower 14 leg are substantially covered with hair strands 18 or follicles.

Figure 2:
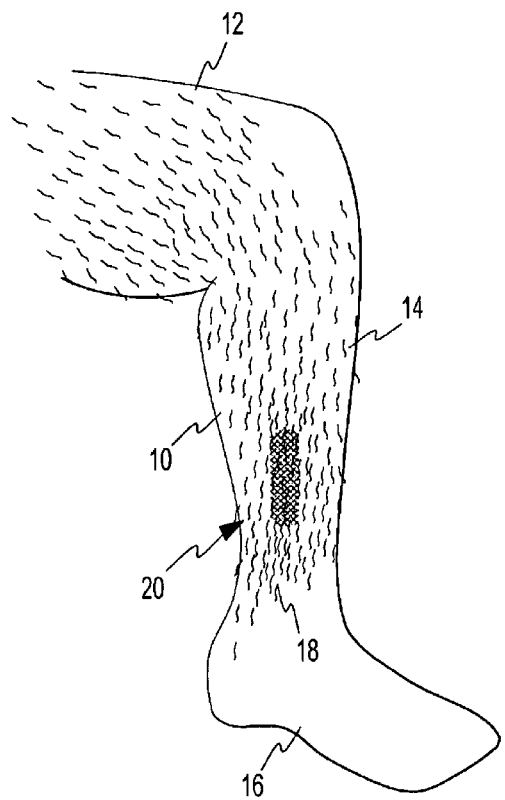
FIG. 2 is a perspective view of a bare leg covered with hair and a portion of hair removal gel composition applied to the lower leg thereof.

Referring to FIG. 2, therein illustrated is a portion of the lower leg 14 covered with an application of the hair removal gel composition 20. The gel composition 20 is comprised of 16 ounces (453.6 grams) of sugar, 3 ounces (85 g) of lemon juice, and 2 ounces (56.7 g) of water. Proportionally, the sugar is present in the approximate ratio of 5.33 parts by weight for each part by weight of lemon juice and 8 parts by weight for each part by weight of water. If desired, various substitutes for lemon juice may be used, such as lime juice or other citrus juices.

The sugar and lemon juice are mixed together in a vessel and heated by a heat source at medium heat (about 200 deg F. at sea level) for about 8 minutes, at which time the water is gradually added and stirred into the mix until a gel-like composition of even consistency is produced. After 6 minutes has elapsed from addition of the water, the vessel is removed from the heat source and cooled to room temperature at which time a consistency that is amenable for application should be achieved. The gel composition 20 is spread onto a part of the leg 10 or other part of the body with unwanted hair 18 by hand or with a utensil, such as a spoon or spatula, in the direction of the hair growth.

Figure 3:
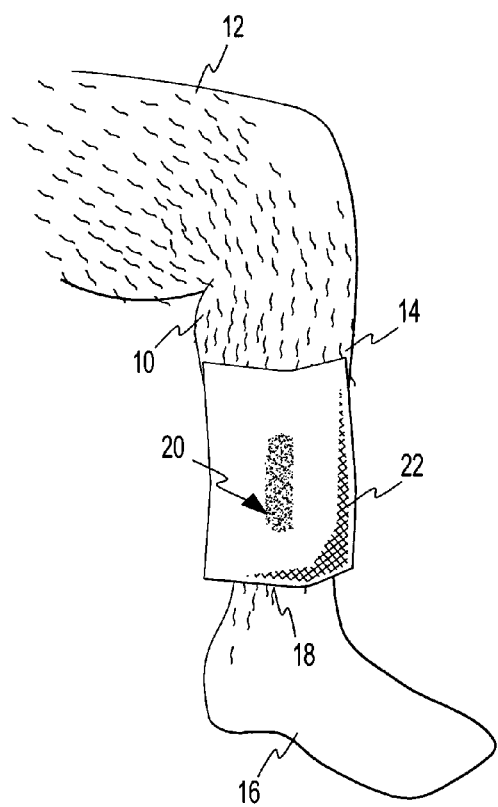
FIG. 3 is a perspective view of a bare leg covered with hair and a woven textile cloth covering and absorbing the hair removal gel composition applied to the lower leg thereof.
Figure 4:
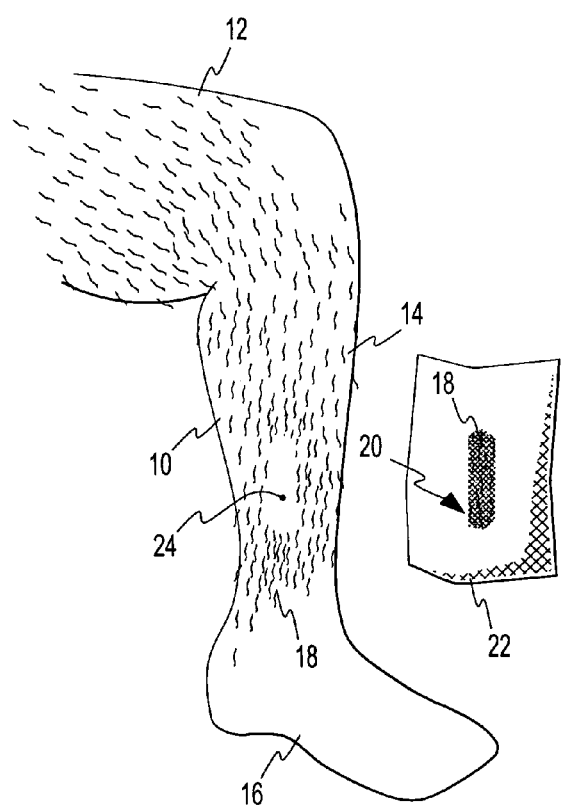
FIG. 4 is a perspective view of a bare leg covered with hair and the woven textile cloth covering and hair removal gel composition absorbed therein removed from the lower leg, thereby revealing the portion of the lower leg rendered hairless by use of the hair removal gel composition.

As shown in FIG. 3, the gel composition 20 is covered with a soft cloth 22 of absorbent material until the cloth 22 has absorbed the gel composition 20, at which time the cloth 20 is ready to be removed from the leg 10. The gel composition 20, absorbed into the cloth 22, dissolves and removes the hair 18 by the roots from the skin, and transfers any remaining hair 18 follicles to the cloth 22 for proper disposal. With the cloth 22 separated from the leg 10 as shown in FIG. 4, a hairless portion 24 of the lower leg 14 is produced. This process can be repeated sequentially until a satisfying amount of hair 18 has been removed from the skin. The process can also be repeated to maintain the desired look at appropriate intervals, e.g. every several weeks. A byproduct of using the gel composition 20 is that it softens the skin, along with a cleansing effect resulting from the removal of dead skin cells.

The ingredients and their amounts can be varied to produce alternate versions of the gel composition 20 in which the basic ingredients of sugar, lemon juice, and water are supplemented by a fragrance comprising either rose water or orange juice. In a first alternate version of the gel composition 20, the ingredients thus consist of:
Sugar—16 ounces (453.6 g)
Lemon Juice—3 ounces (85 g)
Water—2 ounces (56.7 g)
Rose Water—2 drops This mixture equates to sugar's being present in the approximate ratio of 5.33 parts by weight for each part by weight of lemon juice, 8 parts by weight for each part by weight of water, and over 16 parts by weight for each part by weight of rose water.

In a second alternate version, the ingredients consist of:
Sugar—8 ounces (226.8 g)
Lemon Juice—1.5 ounces (42.5 g)
Water—1 ounce (28.3 g)
Rose Water—1 ounce (28.3 g)

This mixture equates to sugar's being present in the approximate ratio of 5.33 parts by weight for each part by weight of lemon juice and 8 parts by weight for each part by weight of water and rose water.

In a third alternate version of the gel composition 20, the ingredients consist of:
Sugar—8 ounces (226.8 g)
Lemon Juice—1 ounce (28.3 g)
Water—1 ounce (28.3 g)
Orange Juice—0.5 ounce (14.2 g)

This mixture equates to sugar's being present in the approximate ratio of 8 parts by weight for each part by weight of lemon juice and water and 16 parts by weight for each part by weight of orange juice.

And, in a fourth alternate version of the gel composition 20, the ingredients thus consist of:
Sugar—16 ounces (453.6 g)
Citrus Juice—3 ounces (85 g)
Water—2 ounces (56.7 g)

This mixture equates to sugar's being present in the approximate ratio of 5.33 parts by weight for each part by weight of citrus juice and 8 parts by weight for each part by weight of water.

The method of mixing and heating the four alternate versions is the same as that described earlier, except that the rose water or orange juice, which provides fragrance, is added to its respective mix of sugar, lemon, lime, or citrus juice, and water immediately before the vessel is removed from the heat source.

While this version of the invention has been illustrated and described in detail in the drawings and foregoing description, the same is to be considered as illustrative and not restrictive in character, it being understood that only the preferred embodiments have been shown and described and that all changes and modifications that come within the spirit of the version of the invention are desired to be protected. With respect to the above description then, it is to be realized that variations in materials, quantity, proportion, and manner of use are deemed readily apparent and obvious to one skilled in the art, and all equivalent relationships to those illustrated in the drawings and described in the specification are intended to be encompassed by the present invention. For instance, various substitutes for lemon juice may be used, such as limejuice or other citrus juices, provided that the substitute is not the equivalent of a second type of citrus juice already being used, such as orange juice.

CONCLUSION AND SCOPE OF INVENTION

From the foregoing, it will be understood by persons skilled in the art that an improved hair removal gel composition has been provided. The invention is relatively simple and easy to manufacture, yet affords a variety of uses. While my description contains many specificities, these should not be construed as limitations on the scope of the version of the invention, but rather as an exemplification of the preferred embodiments thereof. The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to, falling within the scope of the invention. Although this invention has been described in its preferred forms with a certain degree of particularity, it is understood that the present disclosure of the preferred form has been made only by way of example and numerous changes in the details of combination and arrangement of ingredients may be resorted to without departing from the spirit and scope of the invention.

While the invention has been described in connection with the preferred embodiments, it is not intended to limit the scope of the invention to the particular form set forth, but on the contrary, it is intended to cover such alternatives, modifications, and equivalents as may be included within the spirit and scope of the invention as defined by the appended claims.

What is claimed is:

1. A composition for the removal of hair from human skin, wherein the composition is to be applied to a portion of human skin from which the hair is to be removed consisting of:
   226.9 g of sugar;
   28.3 g of lemon juice;
   28.3 g of water; and
   14.2 g of orange juice;
being intermixed and heated to a temperature at which the composition achieves a soft, gel-like consistency before application to human skin.

2. A method for preparing a composition of claim 1 and of applying the composition to a portion of the human skin from which the hair is to be removed, comprising the steps of:
   a) mixing the sugar, lemon juice, and orange juice together in a vessel and heating with a heat source at about 200 degrees F. at sea level for about 8 minutes;
   b) gradually adding water with stirring until a gel-like composition of even consistency is produced;
   c) removing the mixture from the heat source and cooling the mixture to room temperature;
   d) applying said mixture of step (c) to the skin.

3. The method according to claim 2, wherein application of said mixture of step (d) to skin, comprises the steps of:
   a) spreading said mixture of step (d) onto a part of human skin with unwanted hair by hand or a utensil in the direction of hair growth;
   b) placing cloth of soft absorbent material onto said mixture;
   c) allowing said mixture and cloth to remain on said part of human skin for a duration sufficient for said mixture to dissolve unwanted hair;
   d) removing cloth with said mixture and dissolved hair thereon to reveal hairless portion of human skin; and
   e) repeating said steps (a), (b), (c), and (d) to remove a desired quantity of unwanted hair from human skin.

* * * * *

UNITED STATES PATENT AND TRADEMARK OFFICE
CERTIFICATE OF CORRECTION

| | | |
|---|---|---|
| PATENT NO. | : 8,142,766 B1 | Page 1 of 1 |
| APPLICATION NO. | : 12/590538 | |
| DATED | : March 27, 2012 | |
| INVENTOR(S) | : Yasmin Bhatti | |

It is certified that error appears in the above-identified patent and that said Letters Patent is hereby corrected as shown below:

Title Page, Item (54) and at Column 1, line 1, Title should read --Suzaby Hair Removal Gel Composition--.

Signed and Sealed this
First Day of May, 2012

David J. Kappos
*Director of the United States Patent and Trademark Office*